US012805779B2

(12) United States Patent
Compton et al.

(10) Patent No.: US 12,805,779 B2
(45) Date of Patent: Nov. 24, 2026

(54) SYSTEMS AND METHODS FOR ULTRASONICALLY MONITORING URINE OUTPUT

(71) Applicant: C. R. Bard, Inc., Franklin Lakes, NJ (US)

(72) Inventors: Clayton L. Compton, Covington, GA (US); Andrew L. Meyer, Atlanta, GA (US); Matthew R. Tarr, Ponte Vedra, FL (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 376 days.

(21) Appl. No.: 17/879,658

(22) Filed: Aug. 2, 2022

(65) Prior Publication Data

US 2023/0040915 A1 Feb. 9, 2023

Related U.S. Application Data

(60) Provisional application No. 63/230,287, filed on Aug. 6, 2021.

(51) Int. Cl.
*A61B 5/20* (2006.01)
*A61B 5/00* (2006.01)

(52) U.S. Cl.
CPC ............ *A61B 5/208* (2013.01); *A61B 5/0004* (2013.01); *A61B 5/6852* (2013.01); *A61B 5/742* (2013.01); *A61B 2562/0204* (2013.01)

(58) Field of Classification Search
CPC ..... A61B 5/0004; A61B 5/208; A61B 5/6852; A61B 5/742; A61B 2562/0204
See application file for complete search history.

(56) References Cited

U.S. PATENT DOCUMENTS 3,661,143 A 5/1972 Henkin
3,781,920 A 1/1974 Browne et al.
(Continued)

FOREIGN PATENT DOCUMENTS

CA 2882654 A1 10/2007
CN 2445749 Y 9/2001
(Continued)

OTHER PUBLICATIONS

CN 104921738 A English Translation (Year: 2015).*
(Continued)

*Primary Examiner* — Aurelie H Tu
*Assistant Examiner* — Andrew E Hoffpauir
(74) *Attorney, Agent, or Firm* — Rutan & Tucker LLP

(57) ABSTRACT

Disclosed herein is a system for monitoring urine output of a patient. The system includes a collection canister coupled with a display module, the canister having a volume sensor to measure urine output, the measurement may be displayed or transmitted over a network. The system links an identification of the canister to an identification of the patient. A drainage tube is pre-coupled with the canister, and optionally, with the catheter, to define a closed system enclosed in a sterile preconnected tray. The volume sensor includes an ultrasonic sensor configured to detect a distance between the urine level and the top of the canister which is converted into a volume of urine within the canister. The display module is coupled with canister. The canister and the display module each include a console that includes logic stored in memory that, when executed by one or more processors, causes performance of operations.

29 Claims, 6 Drawing Sheets

(56) References Cited

U.S. PATENT DOCUMENTS

| | | | | | |
|---|---|---|---|---|---|
| 3,851,650 | A | | 12/1974 | Darling | |
| 3,919,455 | A | | 11/1975 | Sigdell et al. | |
| 4,276,889 | A | | 7/1981 | Kuntz et al. | |
| 4,286,590 | A | | 9/1981 | Murase | |
| 4,291,692 | A | | 9/1981 | Bowman et al. | |
| 4,296,749 | A | | 10/1981 | Pontifex | |
| 4,305,405 | A | | 12/1981 | Meisch | |
| 4,312,352 | A | * | 1/1982 | Meisch | A61F 5/44 604/322 |
| 4,343,316 | A | | 8/1982 | Jespersen | |
| 4,443,219 | A | | 4/1984 | Meisch et al. | |
| 4,448,207 | A | | 5/1984 | Parrish | |
| 4,509,366 | A | | 4/1985 | Matsushita et al. | |
| 4,532,936 | A | | 8/1985 | LeVeen et al. | |
| 4,658,834 | A | | 4/1987 | Blankenship et al. | |
| 4,712,567 | A | | 12/1987 | Gille et al. | |
| 4,723,950 | A | | 2/1988 | Lee | |
| 4,763,739 | A | | 8/1988 | Kasinoff | |
| 4,834,706 | A | | 5/1989 | Beck et al. | |
| 4,850,375 | A | | 7/1989 | Rosenberg | |
| 4,889,532 | A | | 12/1989 | Metz et al. | |
| 5,002,541 | A | | 3/1991 | Conkling et al. | |
| 5,146,637 | A | | 9/1992 | Bressler et al. | |
| 5,188,327 | A | * | 2/1993 | White | A61G 7/0503 248/314 |
| 5,409,014 | A | | 4/1995 | Napoli et al. | |
| 5,586,085 | A | | 12/1996 | Lichte | |
| 5,725,515 | A | | 3/1998 | Propp | |
| 5,733,319 | A | | 3/1998 | Neilson et al. | |
| 5,738,656 | A | | 4/1998 | Wagner | |
| 5,747,824 | A | | 5/1998 | Jung et al. | |
| 5,769,087 | A | | 6/1998 | Westphal et al. | |
| 5,807,278 | A | | 9/1998 | McRae | |
| 5,823,972 | A | | 10/1998 | McRae | |
| 5,891,051 | A | | 4/1999 | Han et al. | |
| 5,911,786 | A | | 6/1999 | Nielsen et al. | |
| 6,129,684 | A | | 10/2000 | Sippel et al. | |
| 6,132,407 | A | | 10/2000 | Genese et al. | |
| 6,175,977 | B1 | | 1/2001 | Schumacher et al. | |
| 6,250,152 | B1 | | 6/2001 | Klein et al. | |
| 6,256,532 | B1 | | 7/2001 | Cha | |
| 6,261,254 | B1 | | 7/2001 | Baron et al. | |
| 6,434,418 | B1 | | 8/2002 | Neal et al. | |
| 6,454,372 | B1 | | 9/2002 | Yang | |
| 6,579,247 | B1 | | 6/2003 | Abramovitch et al. | |
| 6,592,612 | B1 | | 7/2003 | Samson et al. | |
| 6,709,420 | B1 | | 3/2004 | Lincoln et al. | |
| 6,716,200 | B2 | | 4/2004 | Bracken et al. | |
| 7,011,634 | B2 | | 3/2006 | Paasch et al. | |
| 7,161,484 | B2 | | 1/2007 | Tsoukalis | |
| 7,211,037 | B2 | | 5/2007 | Briggs et al. | |
| 7,437,945 | B1 | | 10/2008 | Feller | |
| 7,442,754 | B2 | | 10/2008 | Tepper et al. | |
| 7,722,584 | B2 | | 5/2010 | Tanaka et al. | |
| 7,739,907 | B2 | | 6/2010 | Boiarski | |
| 7,871,385 | B2 | | 1/2011 | Levinson | |
| 7,931,630 | B2 | | 4/2011 | Nishtala et al. | |
| 7,976,533 | B2 | | 7/2011 | Larsson | |
| 7,998,126 | B1 | | 8/2011 | Fernandez | |
| 8,295,933 | B2 | | 10/2012 | Gerber et al. | |
| 8,328,733 | B2 | | 12/2012 | Forte et al. | |
| 8,328,734 | B2 | | 12/2012 | Salvadori et al. | |
| 8,337,476 | B2 | | 12/2012 | Greenwald et al. | |
| 8,374,688 | B2 | | 2/2013 | Libbus et al. | |
| 8,403,884 | B2 | | 3/2013 | Nishtala | |
| 8,471,231 | B2 | | 6/2013 | Paz | |
| 8,663,128 | B2 | | 3/2014 | Paz et al. | |
| 8,773,259 | B2 | | 7/2014 | Judy et al. | |
| 8,790,277 | B2 | | 7/2014 | Elliott et al. | |
| 8,790,320 | B2 | | 7/2014 | Christensen | |
| 8,790,577 | B2 | | 7/2014 | Mizumoto et al. | |
| 8,813,551 | B2 | | 8/2014 | Boiarski | |
| 8,827,924 | B2 | | 9/2014 | Paz et al. | |
| 8,832,558 | B2 | | 9/2014 | Cardarelli et al. | |
| 8,900,196 | B2 | | 12/2014 | Andino | |
| 9,045,887 | B2 | | 6/2015 | O'Malley | |
| 9,050,046 | B2 | | 6/2015 | Elliott et al. | |
| 9,074,920 | B2 | | 7/2015 | Mendels et al. | |
| 9,216,242 | B2 | | 12/2015 | Nishtala et al. | |
| 9,480,821 | B2 | | 11/2016 | Ciccone et al. | |
| 9,592,034 | B2 | | 3/2017 | Hall et al. | |
| 9,642,987 | B2 | | 5/2017 | Bierman et al. | |
| 9,731,097 | B2 | | 8/2017 | Andino et al. | |
| 9,848,827 | B1 | | 12/2017 | LaBorde | |
| 9,895,095 | B2 | | 2/2018 | Chen | |
| 9,928,341 | B2 | | 3/2018 | Angelides | |
| 9,962,516 | B2 | | 5/2018 | Lampotang et al. | |
| 10,071,202 | B2 | | 9/2018 | Handler | |
| 10,182,747 | B2 | | 1/2019 | Charlez et al. | |
| 10,245,008 | B2 | | 4/2019 | Paige | |
| 10,301,807 | B1 | | 5/2019 | Kolesar | |
| 10,362,981 | B2 | | 7/2019 | Paz et al. | |
| 10,383,606 | B1 | | 8/2019 | McCord et al. | |
| 10,448,875 | B2 | | 10/2019 | Holt et al. | |
| 10,722,679 | B2 | | 7/2020 | Lampotang et al. | |
| 10,799,386 | B1 | | 10/2020 | Harrison, Sr. | |
| 10,881,320 | B2 | | 1/2021 | Duval et al. | |
| 10,881,778 | B2 | | 1/2021 | Scarpaci et al. | |
| 11,291,577 | B2 | | 4/2022 | Seres et al. | |
| 11,473,958 | B2 | | 10/2022 | Holt et al. | |
| 11,540,760 | B1 | | 1/2023 | Guillemette | |
| 11,654,042 | B2 | | 5/2023 | Hughett, Sr. | |
| 11,703,365 | B2 | | 7/2023 | Tourchak et al. | |
| 12,083,261 | B2 | | 9/2024 | Justice et al. | |
| 12,109,353 | B2 | | 10/2024 | Cheng et al. | |
| 12,364,423 | B2 | | 7/2025 | Cheng et al. | |
| 12,408,853 | B2 | | 9/2025 | Kriscovich et al. | |
| 2001/0056226 | A1 | | 12/2001 | Zodnik et al. | |
| 2002/0013518 | A1 | | 1/2002 | West et al. | |
| 2002/0016719 | A1 | | 2/2002 | Nemeth et al. | |
| 2002/0161314 | A1 | | 10/2002 | Sarajarvi | |
| 2002/0193760 | A1 | | 12/2002 | Thompson | |
| 2003/0000303 | A1 | | 1/2003 | Livingston et al. | |
| 2003/0140697 | A1 | | 7/2003 | Van Ee | |
| 2003/0163183 | A1 | | 8/2003 | Carson | |
| 2003/0163287 | A1 | | 8/2003 | Vock et al. | |
| 2004/0176747 | A1 | | 9/2004 | Feneley | |
| 2004/0267086 | A1 | | 12/2004 | Anstadt et al. | |
| 2005/0020958 | A1 | | 1/2005 | Paolini et al. | |
| 2005/0065583 | A1 | | 3/2005 | Voorhees et al. | |
| 2005/0172712 | A1 | | 8/2005 | Nyce | |
| 2005/0247121 | A1 | | 11/2005 | Pelster | |
| 2006/0065713 | A1 | | 3/2006 | Kingery | |
| 2006/0100743 | A1 | | 5/2006 | Townsend et al. | |
| 2006/0253091 | A1 | | 11/2006 | Vernon | |
| 2006/0291533 | A1 | * | 12/2006 | Faries | A61J 1/1462 374/E11.018 |
| 2007/0010797 | A1 | | 1/2007 | Nishtala et al. | |
| 2007/0078444 | A1 | | 4/2007 | Larsson | |
| 2007/0106177 | A1 | | 5/2007 | Hama | |
| 2007/0145137 | A1 | | 6/2007 | Mrowiec | |
| 2007/0225668 | A1 | | 9/2007 | Otto | |
| 2007/0252714 | A1 | | 11/2007 | Rondoni et al. | |
| 2008/0027409 | A1 | | 1/2008 | Rudko et al. | |
| 2008/0217391 | A1 | * | 9/2008 | Roof | G16H 10/65 235/494 |
| 2008/0312550 | A1 | * | 12/2008 | Nishtala | A61B 5/20 600/549 |
| 2008/0312556 | A1 | | 12/2008 | Dijkman | |
| 2009/0056020 | A1 | | 3/2009 | Caminade et al. | |
| 2009/0099629 | A1 | | 4/2009 | Carson et al. | |
| 2009/0157430 | A1 | | 6/2009 | Rule et al. | |
| 2009/0171169 | A1 | | 7/2009 | Nagata | |
| 2009/0287170 | A1 | * | 11/2009 | Otto | A61B 5/20 604/327 |
| 2009/0315684 | A1 | | 12/2009 | Sacco et al. | |
| 2010/0064426 | A1 | | 3/2010 | Chikara Imamura | |
| 2010/0094204 | A1 | | 4/2010 | Nishtala | |
| 2010/0122963 | A1 | | 5/2010 | Costa et al. | |
| 2010/0130949 | A1 | | 5/2010 | Garcia | |
| 2010/0137743 | A1 | | 6/2010 | Nishtala et al. | |
| 2010/0214106 | A1 | * | 8/2010 | Braun | A61M 5/1684 340/618 |
| 2010/0262047 | A1 | | 10/2010 | Genis | |

(56) References Cited

U.S. PATENT DOCUMENTS

2011/0113540 A1 5/2011 Plate et al.
2011/0120219 A1 5/2011 Barlesi et al.
2011/0178425 A1 7/2011 Nishtala et al.
2011/0224636 A1 9/2011 Keisic
2011/0230824 A1 9/2011 Salinas et al.
2011/0238042 A1 9/2011 Davis et al.
2011/0251572 A1 10/2011 Nishtala et al.
2011/0263952 A1 10/2011 Bergman et al.
2012/0029408 A1 2/2012 Beaudin
2012/0035496 A1 2/2012 Denison et al.
2012/0059286 A1 3/2012 Hastings et al.
2012/0078137 A1 3/2012 Mendels et al.
2012/0078235 A1 3/2012 Martin et al.
2012/0095304 A1 4/2012 Biondi
2012/0108917 A1 5/2012 Libbus et al.
2012/0109008 A1 5/2012 Charlez et al.
2012/0118650 A1 5/2012 Gill
2012/0123233 A1 5/2012 Cohen
2012/0127103 A1 5/2012 Qualey et al.
2012/0226196 A1 9/2012 DiMino et al.
2012/0234434 A1 9/2012 Woodruff et al.
2012/0302917 A1 11/2012 Fitzgerald et al.
2012/0323144 A1 12/2012 Coston et al.
2012/0323502 A1 12/2012 Tanoura et al.
2013/0030262 A1 1/2013 Burnett et al.
2013/0066166 A1 3/2013 Bumett et al.
2013/0109927 A1 5/2013 Menzel
2013/0109928 A1 5/2013 Menzel
2013/0131610 A1 5/2013 Dewaele et al.
2013/0218106 A1 8/2013 Coston et al.
2013/0245498 A1 9/2013 Delaney et al.
2013/0256486 A1* 10/2013 Taylor .................. A61G 7/0503
248/231.71
2013/0267871 A1 10/2013 Delaney et al.
2013/0304061 A1 11/2013 Chang et al.
2014/0039348 A1 2/2014 Bullington et al.
2014/0155781 A1 6/2014 Bullington et al.
2014/0155782 A1 6/2014 Bullington et al.
2014/0159921 A1 6/2014 Qualey et al.
2014/0166691 A1 6/2014 Chen et al.
2014/0187666 A1 7/2014 Aizenberg et al.
2014/0207085 A1 7/2014 Brandt et al.
2014/0228755 A1 8/2014 Darrah et al.
2014/0243635 A1 8/2014 Arefieg
2014/0335490 A1 11/2014 Baarman et al.
2015/0120321 A1 4/2015 David et al.
2015/0233749 A1 8/2015 Wang et al.
2015/0342576 A1 12/2015 Hall et al.
2015/0343173 A1 12/2015 Tobescu et al.
2015/0359522 A1 12/2015 Recht et al.
2015/0362351 A1 12/2015 Joshi et al.
2016/0051176 A1* 2/2016 Ramos .................. G01F 23/265
600/573
2016/0051177 A1 2/2016 Chen
2016/0136356 A1 5/2016 Ribble et al.
2016/0183819 A1 6/2016 Burnett et al.
2016/0374874 A1 12/2016 Trepanier et al.
2017/0035342 A1 2/2017 Elia et al.
2017/0043089 A1 2/2017 Handler
2017/0100068 A1 4/2017 Kostov
2017/0113000 A1 4/2017 Tobescu et al.
2017/0136209 A1 5/2017 Burnett et al.
2017/0140103 A1 5/2017 Angelides
2017/0196478 A1 7/2017 Hunter
2017/0202698 A1 7/2017 Zani et al.
2017/0241978 A1 8/2017 Duval
2017/0249445 A1 8/2017 Devries et al.
2017/0290540 A1 10/2017 Franco
2017/0291012 A1 10/2017 Iglesias
2017/0307423 A1 10/2017 Pahwa et al.
2017/0322197 A1 11/2017 Hall et al.
2018/0015251 A1 1/2018 Lampotang et al.
2018/0110455 A1 4/2018 Chang et al.
2018/0110456 A1 4/2018 Cooper et al.
2018/0160961 A1 6/2018 Gopinathan et al.
2018/0214122 A1 8/2018 Ansell et al.
2018/0214297 A1* 8/2018 Hughett ............... A61B 5/7445
2018/0245967 A1* 8/2018 Parker .................... G01G 19/18
2018/0280236 A1 10/2018 Ludin et al.
2018/0306661 A1 10/2018 Stacey
2018/0317891 A1 11/2018 Kim
2018/0344234 A1 12/2018 McKinney et al.
2018/0344295 A1 12/2018 Leibman
2019/0006047 A1 1/2019 Gorek et al.
2019/0017535 A1 1/2019 Ormsbee et al.
2019/0046102 A1 2/2019 Kushnir et al.
2019/0069829 A1 3/2019 Bulut
2019/0069830 A1 3/2019 Holt et al.
2019/0126006 A1 5/2019 Rehm et al.
2019/0150821 A1 5/2019 Waters et al.
2019/0167144 A1 6/2019 Jung et al.
2019/0201596 A1 7/2019 Luxon et al.
2019/0218826 A1 7/2019 Allen et al.
2019/0223844 A1 7/2019 Aboagye et al.
2019/0231244 A1 8/2019 Swan et al.
2019/0247236 A1 8/2019 Sides et al.
2019/0254582 A1 8/2019 Wei et al.
2019/0298317 A1 10/2019 Colgan et al.
2019/0321588 A1 10/2019 Burnett et al.
2019/0328945 A1 10/2019 Analytis et al.
2019/0343445 A1 11/2019 Burnett et al.
2019/0358387 A1 11/2019 Elbadry et al.
2019/0365308 A1 12/2019 Laing et al.
2019/0381223 A1 12/2019 Culbert et al.
2020/0022637 A1 1/2020 Kurzrock et al.
2020/0064172 A1 2/2020 Tabaczewski et al.
2020/0085378 A1 3/2020 Burnett et al.
2020/0121300 A1 4/2020 Moore
2020/0187863 A1 6/2020 Tu et al.
2020/0254178 A1 8/2020 Halpert et al.
2020/0268302 A1 8/2020 Oh
2020/0268303 A1 8/2020 Oliva
2020/0289749 A1 9/2020 Odashima et al.
2020/0405524 A1 12/2020 Gill
2021/0000361 A1 1/2021 Lark et al.
2021/0054610 A1 2/2021 Hall et al.
2021/0077007 A1 3/2021 Jouret et al.
2021/0098124 A1 4/2021 Crook et al.
2021/0100533 A1* 4/2021 Seres ....................... A61B 5/42
2021/0113130 A1 4/2021 Tran
2021/0202084 A1 7/2021 Cronin et al.
2021/0298653 A1 9/2021 Woodard et al.
2021/0299353 A1 9/2021 Mannu et al.
2021/0361211 A1 11/2021 Teramoto et al.
2022/0018692 A1 1/2022 Tourchak et al.
2022/0026001 A1 1/2022 Cheng et al.
2022/0026261 A1 1/2022 Funnell et al.
2022/0079487 A1 3/2022 Horiguchi et al.
2022/0192564 A1 6/2022 Kriscovich et al.
2022/0192565 A1 6/2022 Cheng et al.
2022/0192566 A1 6/2022 Cheng et al.
2022/0193375 A1 6/2022 Rehm et al.
2022/0233120 A1 7/2022 Beuret et al.
2022/0296140 A1 9/2022 Nguyen et al.
2022/0296406 A1 9/2022 Keelen
2022/0330867 A1 10/2022 Conley et al.
2022/0386917 A1 12/2022 Mann et al.
2023/0000259 A1* 1/2023 Taylor .................... H04R 1/026
2023/0019703 A1 1/2023 Behzad et al.
2023/0022547 A1 1/2023 Cho et al.
2023/0024494 A1 1/2023 Tang et al.
2023/0025333 A1 1/2023 Patel et al.
2023/0028966 A1 1/2023 Franano
2023/0035669 A1 2/2023 Raja et al.
2023/0058553 A1 2/2023 Fallows et al.
2023/0060232 A1 3/2023 Patel et al.
2023/0084476 A1 3/2023 Robichaud et al.
2023/0089041 A1 3/2023 Handler
2024/0042120 A1 2/2024 Cheng et al.
2024/0081708 A1 3/2024 Kelly et al.
2024/0108268 A1 4/2024 Woodard et al.
2024/0252783 A1 8/2024 Waitkus et al.
2024/0347162 A1 10/2024 Meese et al.
2024/0360938 A1 10/2024 Cheng et al.

(56) References Cited

U.S. PATENT DOCUMENTS

| | | | |
|---|---|---|---|
| 2024/0424186 | A1 | 12/2024 | Justice et al. |
| 2025/0090066 | A1 | 3/2025 | Tourchak |
| 2025/0120636 | A1 | 4/2025 | Compton et al. |
| 2025/0205456 | A1 | 6/2025 | Rehm et al. |
| 2025/0339073 | A1 | 11/2025 | Cheng et al. |
| 2026/0000330 | A1 | 1/2026 | Kriscovich et al. |
| 2026/0033762 | A1 | 2/2026 | Fallows et al. |
| 2026/0183468 | A1 | 7/2026 | Cheng et al. |

FOREIGN PATENT DOCUMENTS

| | | | |
|---|---|---|---|
| CN | 200951235 | Y | 9/2007 |
| CN | 201492414 | U | 6/2010 |
| CN | 102647939 | A | 8/2012 |
| CN | 103054559 | B | 5/2015 |
| CN | 104921738 | A * | 9/2015 |
| CN | 205306875 | U | 6/2016 |
| CN | 107952140 | A | 4/2018 |
| CN | 109498013 | A | 3/2019 |
| CN | 110859636 | A | 3/2020 |
| CN | 112426156 | A | 3/2021 |
| EP | 0342028 | A2 | 11/1989 |
| ES | 2760470 | T3 | 5/2020 |
| GB | 2437549 | A | 10/2007 |
| GB | 2576743 | A | 3/2020 |
| JP | S49-75171 | A | 7/1974 |
| JP | S54-147066 | A | 11/1979 |
| JP | S58-190719 | A | 11/1983 |
| JP | S60-219517 | A | 11/1985 |
| JP | H02-057240 | B2 | 12/1990 |
| JP | H08-271301 | A | 10/1996 |
| JP | H10-104041 | A | 4/1998 |
| JP | 2007-303982 | A | 11/2007 |
| JP | 2008-524618 | A | 7/2008 |
| JP | 2009-068959 | A | 4/2009 |
| JP | 2010-121950 | A | 6/2010 |
| JP | 2010-530978 | A | 9/2010 |
| JP | 2012-105947 | A | 6/2012 |
| JP | 2012-225790 | A | 11/2012 |
| JP | 2018108356 | A | 7/2018 |
| KR | 20070115495 | A | 12/2007 |
| NL | 2013740 | A | 8/2016 |
| RU | 2615727 | C2 | 4/2017 |
| WO | 1981003427 | A1 | 12/1981 |
| WO | 2004045410 | A1 | 6/2004 |
| WO | 2013013782 | A2 | 1/2013 |
| WO | 20130178742 | A1 | 12/2013 |
| WO | 2014/043650 | A2 | 3/2014 |
| WO | 2014105755 | A1 | 7/2014 |
| WO | 2014108690 | A1 | 7/2014 |
| WO | 2014/135856 | A1 | 9/2014 |
| WO | 2014/151068 | A2 | 9/2014 |
| WO | 2014145971 | A2 | 9/2014 |
| WO | 201511402 | A1 | 1/2015 |
| WO | 2015/105916 | A1 | 7/2015 |
| WO | 2015/127390 | A1 | 8/2015 |
| WO | 2015191125 | A1 | 12/2015 |
| WO | 2016177901 | A1 | 11/2016 |
| WO | 2017/023794 | A1 | 2/2017 |
| WO | 2018156624 | A1 | 8/2018 |
| WO | 2019066357 | A1 | 4/2019 |
| WO | 2019106675 | A1 | 6/2019 |
| WO | 2019/226697 | A1 | 11/2019 |
| WO | 2020033752 | A1 | 2/2020 |
| WO | 2020154370 | A1 | 7/2020 |
| WO | 2020251893 | A1 | 12/2020 |
| WO | 2022108589 | A1 | 5/2022 |
| WO | 2022182794 | A1 | 9/2022 |
| WO | 2023022895 | A1 | 2/2023 |
| WO | 2023027871 | A1 | 3/2023 |
| WO | 2023076067 | A1 | 5/2023 |

OTHER PUBLICATIONS

PCT/US20/61367 filed Nov. 19, 2020 International Search Report and Written Opinion dated Feb. 22, 2021.

U.S. Appl. No. 17/262,080, filed Jan. 21, 2021 Non-Final Office Action dated Apr. 6, 2023.

U.S. Appl. No. 17/556,907, filed Dec. 20, 2021 Restriction Requirement dated May 12, 2023.

EP 23188337.2 filed May 21, 2019 Extended European Search Report dated Dec. 4, 2023.

PCT/US2019/033389 filed Nov. 26, 2020 Extended European Search Report dated Jun. 4, 2021.

U.S. Appl. No. 17/054,493, filed Nov. 10, 2020 Final Office Action dated Oct. 4, 2023.

U.S. Appl. No. 17/054,493, filed Nov. 10, 2020 Notice of Allowance dated Jan. 4, 2024.

U.S. Appl. No. 17/262,080, filed Jan. 21, 2021 Notice of Allowance dated Oct. 13, 2023.

U.S. Appl. No. 17/306,821, filed May 3, 2021 Advisory Action dated Oct. 3, 2023.

U.S. Appl. No. 17/373,546, filed Jul. 12, 2021 Non-Final Office Action dated Nov. 1, 2023.

U.S. Appl. No. 17/556,907, filed Dec. 20, 2021 Notice of Allowance dated Dec. 6, 2023.

"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).

U.S. Appl. No. 17/552,250, filed Dec. 15, 2021 Non-Final Office Action dated Sep. 19, 2024.

U.S. Appl. No. 17/556,931, filed Dec. 20, 2021 Final Office Action dated Oct. 1, 2024.

DFree Personal—Consumer Product Brochure, 2019.

DFree Pro Brochure 2019.

Leonhäuser, D. et al., "Evaluation of electrical impedance tomography for determination of urinary bladder volume comparison with standard ultrasound methods in healthy volunteers."—BioMed Engr On-line; 17:95; 2018.

Li, R., et al., "Design of a Noninvasive Bladder Urinary Volume Monitoring System Based on Bio-Impedance."—Engineering; vol. 5; pp. 321-325; 2013.

PCT/US2022/017574 filed Feb. 23, 2022 Internation Search Report and Written Opinion dated Jun. 8, 2022.

Reichmuth, M., et al., "A Non-invasive Wearable Bioimpedance System to Wirelessly Monitor Bladder Filling."—Dep. of Health Sciences and Technology1'Department of Information Technology and Electrical Engineering ETH Zurich, Zurich, Switzerland—Conference Paper; Mar. 2020.

Schlebusch, T. et al., "Bladder Volume estimation from electrical impedance tomography" Physiological Measurement, Institute of Physics, Bristol, GB. vol. 35 No. 9 Aug. 20, 2014. (Aug. 20, 2014).

SECA product catalog, https://us.secashop.com/products/seca-mbca/seca-mbca-514/5141321139, last accessed Sep. 11, 2020.

U.S. Appl. No. 17/262,080, filed Jan. 21, 2021 Final Office Action dated Sep. 11, 2023.

U.S. Appl. No. 17/306,821, filed May 3, 2021 Final Office Action dated Jul. 19, 2023.

U.S. Appl. No. 17/556,907, filed Dec. 20, 2021 Non-Final Office Action dated Aug. 17, 2023.

EP 20962628.2 filed May 31, 2023 Extended European Search Report dated Apr. 20, 2024.

PCT/US2022/039191 filed Aug. 2, 2022 International Search Report and Written Opinion dated Dec. 5, 2022.

PCT/US2022/039746 filed Aug. 8, 2022 International Search Report and Written Opinion dated Nov. 18, 2022.

PCT/US2022/046920 filed Oct. 17, 2022 International Search Report and Written Opinion dated Feb. 20, 2023.

U.S. Appl. No. 17/306,821, filed May 3, 2021 Notice of Allowance dated Apr. 23, 2024.

U.S. Appl. No. 17/373,546, filed Jul. 12, 2021 Notice of Allowance dated Mar. 7, 2024.

(56) References Cited

OTHER PUBLICATIONS

U.S. Appl. No. 17/373,546, filed Jul. 12, 2021 Notice of Allowance dated May 29, 2024.
U.S. Appl. No. 17/556,931, filed Dec. 20, 2021 Non-Final Office Action dated Mar. 27, 2024.
U.S. Appl. No. 17/556,931, filed Dec. 20, 2021 Restriction Requirement dated Feb. 22, 2024.
U.S. Appl. No. 15/748,107, filed Jan. 26, 2018 Notice of Allowance dated Dec. 12, 2022.
U.S. Appl. No. 17/054,493, filed Nov. 10, 2020 Non-Final Office Action dated Jan. 27, 2023.
U.S. Appl. No. 17/3026,821, filed May 3, 2021 Non-Final Office Action dated Jan. 10, 2023.
U.S. Appl. No. 17/373,535, filed Jul. 12, 2021 Non-Final Office Action dated Nov. 9, 2022.
U.S. Appl. No. 17/373,535, filed Jul. 12, 2021 Notice of Allowance dated Feb. 23, 2023.
Bard Medical, Criticore Disposables—Non I.C., 3 pages, www.bardmedical.com/products/patienl-moniloring-,ystems/criticore®-system/criticore®-disposables-non-ic/ Jan. 30, 2015.
Bard Medical, Criticore Infection Control Disposables, 3 pages, www.bardmedical.com/patienl-moniloring-,ystems/criticore®-system/criticore®-infection-control-disposables/ Jan. 30, 2015.
Bard Medical, Criticore Monitor, 11 pages, www.bardmedical.com/products/patient-monitoring-systems/criticore®-monitor/ Jan. 30, 2015.
Bard Medical, Urine Meiers, 3 pages, www.bardmedical.com/products/urological-drainage/urine-collection/urinemeters/Jan. 30, 2015.
Biometrix, Urimetrix, 4 pages, www.biometrixmedical.com/Products/56/Urimetrix%E2%84%A2 Oct. 29, 2014.
Observe Medical, sippi, 3 pages, www.observemedical.com/products.html Oct. 29, 2014.
PCT/US19/33389 filed May 21, 2019 International Search Report and Written Opinion dated Aug. 2, 2019.
PCT/US2016/044835 filed Jul. 20, 2016 International Search Report and Written Opinion dated Dec. 16, 2016.
PCT/US2019/045787 filed Aug. 8, 2019 International Preliminary Report on Patentability dated Feb. 16, 2021.
PCT/US2019/045787 filed Aug. 8, 2019 International Search Report and Written Opinion dated Oct. 2, 2019.
U.S. Appl. No. 17/054,493, filed Nov. 10, 2020 Final Office Action dated May 31, 2022.
U.S. Appl. No. 15/748,107, filed Jan. 26, 2018 Final Office Action dated Dec. 23, 2020.
U.S. Appl. No. 15/748,107, filed Jan. 26, 2018 Final Office Action dated Feb. 7, 2022.
U.S. Appl. No. 15/748,107, filed Jan. 26, 2018 Non-Final Office Action dated Sep. 3, 2021.
U.S. Appl. No. 15/748,107, filed Jan. 26, 2018 Non-Final Office Action dated Sep. 4, 2020.
U.S. Appl. No. 17/054,493, filed Nov. 10, 2020 Non-Final Office Action dated Nov. 24, 2021.
"Volumetric Flow Rate", www.vcalc.com/wiki/JeffNolumetric+%28Fluid%29+Flow+Rate, accessed Jan. 9, 2025, created Mar. 8, 2018 (Year: 2018).
U.S. Appl. No. 17/552,250, filed Dec. 15, 2021 Final Office Action dated Feb. 11, 2025.
U.S. Appl. No. 17/556,931, filed Dec. 20, 2021 Advisory Action dated Dec. 6, 2024.
U.S. Appl. No. 17/560,079, filed Dec. 22, 2021 Notice of Allowance dated Oct. 29. 2024.
U.S. Appl. No. 17/587,938, filed Jan. 28, 2022 Restriction Requirement dated Jan. 22, 2025.
U.S. Appl. No. 17/833,682, filed Jun. 6, 2022 Non-Final Office Action dated Jan. 15, 2025.
U.S. Appl. No. 17/870,698, filed Jul. 21, 2022 Restriction Requirement dated Feb. 12, 2025.
U.S. Appl. No. 17/893,435, filed Aug. 23, 2022 Non-Final Office Action dated Jan. 17, 2025.
U.S. Appl. No. 17/552,250, filed Dec. 15, 2021 Advisory Action dated May 8, 2025.
U.S. Appl. No. 17/552,250, filed Dec. 15, 2021 Notice of Allowance dated May 20, 2025.
U.S. Appl. No. 17/556,931, filed Dec. 20, 2021 Notice of Allowance dated Mar. 18, 2025.
U.S. Appl. No. 17/587,938, filed Jan. 28, 2022 Non-Final Office Action dated May 12, 2025.
U.S. Appl. No. 17/682,785, filed Feb. 28, 2022 Restriction Requirement dated Apr. 2, 2025.
U.S. Appl. No. 17/833,682, filed Jun. 6, 2022 Final Office Action dated May 12, 2025.
U.S. Appl. No. 17/863,223, filed Jul. 12, 2022 Non-Final Office Action dated Apr. 2, 2025.
U.S. Appl. No. 17/863,923, filed Jul. 13, 2022 Restriction Requirement dated May 21, 2025.
U.S. Appl. No. 17/870,698, filed Jul. 21, 2022 Non-Final Office Action dated Apr. 9, 2025.
U.S. Appl. No. 17/873,834, filed Jul. 26, 2022 Non-Final Office Action dated May 19, 2025.
U.S. Appl. No. 17/883,507, filed Aug. 8, 2022 Restriction Requirement dated May 19, 2025.
U.S. Appl. No. 17/941,941, filed Sep. 9, 2022 Restriction Requirement dated May 28, 2025.
U.S. Appl. No. 18/278,167, filed Aug. 21, 2023 Non-Final Office Action dated Apr. 24, 2025.
U.S. Appl. No. 17/682,785, filed Feb. 28, 2022 Non-Final Office Action dated Jul. 16, 2025.
U.S. Appl. No. 17/870,698, filed Jul. 21, 2022 Final Office Action dated Jul. 29, 2025.
U.S. Appl. No. 17/893,435, filed Aug. 23, 2022 Notice of Allowance dated Jul. 11, 2025.
U.S. Appl. No. 18/036,335, filed May 10, 2023 Non-Final Office Action dated Jun. 18, 2025.
U.S. Appl. No. 18/682,075, filed Feb. 7, 2024 Non-Final Office Action dated Jun. 18, 2025.
U.S. Appl. No. 17/833,682, filed Jun. 6, 2022 Non-Final Office Action dated Sep. 15, 2025.
U.S. Appl. No. 17/863,223, filed Jul. 12, 2022 Final Office Action dated Sep. 24, 2025.
U.S. Appl. No. 17/863,923, filed Jul. 13, 2022 Non-Final Office Action dated Oct. 22, 2025.
U.S. Appl. No. 17/883,507, filed Aug. 8, 2022 Non-Final Office Action dated Aug. 27, 2025.
U.S. Appl. No. 17/941,941, filed Sep. 9, 2022 Non-Final Office Action dated Aug. 22, 2025.
U.S. Appl. No. 18/036,335, filed May 10, 2023 Notice of Allowance dated Oct. 21, 2025.
U.S. Appl. No. 18/278,167, filed Aug. 21, 2023 Notice of Allowance dated Oct. 16, 2025.
Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, accessed Sep. 10, 2025 (Year: 2021).
Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, translated via Google Translate, accessed Sep. 10, 2025 (Year:2025).
U.S. Appl. No. 17/682,785, filed Feb. 28, 2022 Final Office Action dated Jan. 9, 2026.
U.S. Appl. No. 17/833,682, filed Jun. 6, 2022 Final Office Action dated Jan. 16, 2026.
U.S. Appl. No. 17/863,223, filed Jul. 12, 2022 Advisory Action dated Dec. 1, 2025.
U.S. Appl. No. 17/863,923, filed Jul. 13, 2022 Notice of Allowance dated Feb. 27, 2026.
U.S. Appl. No. 17/870,698, filed Jul. 21, 2022 Non-Final Office Action dated Nov. 21, 2025.
U.S. Appl. No. 17/873,834, filed Jul. 26, 2022 Advisory Action dated Jan. 30, 2026.
U.S. Appl. No. 17/873,834, filed Jul. 26, 2022 Final Office Action dated Nov. 28, 2025.
U.S. Appl. No. 17/941,941, filed Sep. 9, 2022 Final Office Action dated Jan. 30, 2026.

(56) References Cited

OTHER PUBLICATIONS

U.S. Appl. No. 18/682,075, filed Feb. 7, 2024 Advisory Action dated Mar. 6, 2026.
U.S. Appl. No. 18/682,082, filed Feb. 7, 2024 Non-Final Office Action dated Feb. 11, 2026.
U.S. Appl. No. 17/833,682, filed Jun. 6, 2022 Advisory Action dated Mar. 24, 2026.
U.S. Appl. No. 17/863,223, filed Jul. 12, 2022 Non-Final Office Action dated Apr. 21, 2026.
U.S. Appl. No. 17/873,834, filed Jul. 26, 2022 Non-Final Office Action dated Mar. 12, 2026.
U.S. Appl. No. 17/941,941, filed Sep. 9, 2022 Advisory Action dated Apr. 7, 2026.
U.S. Appl. No. 18/538,136, filed Dec. 13, 2023 Restriction Requirement dated May 14, 2026.
U.S. Appl. No. 18/612,745, filed Mar. 21, 2024 Non-Final Office Action dated Apr. 1, 2026.
U.S. Appl. No. 18/701,916, filed Apr. 16, 2024 Non-Final Office Action dated Mar. 23, 2026.
U.S. Appl. No. 18/765,516, filed Jul. 8, 2024 Non-Final Office Action dated May 21, 2026.
Wilson NPL SWIR Imaging 101 https://~wilson.com/swir-imaging-101-what-can-it-do-for-you/ Jan. 2021 (Year: 2021).
EP 26162487.8 filed Mar. 5, 2026 Extended European Search Report dated Jul. 9, 2026.
U.S. Appl. No. 17/682,785, filed Feb. 28, 2022 Notice of Allowance dated Jun. 30, 2026.
U.S. Appl. No. 17/833,682, filed Jun. 6, 2022 Notice of Allowance dated Aug. 18, 2026.
U.S. Appl. No. 17/870,698, filed Jul. 21, 2022 Final Office Action dated Jun. 17, 2026.
U.S. Appl. No. 17/873,834, filed Jul. 26, 2022 Notice of Allowance dated Jul. 21, 2026.
U.S. Appl. No. 17/941,941, filed Sep. 9, 2022 Non-Final Office Action dated Jun. 25, 2026.
U.S. Appl. No. 18/538,136 filed Dec. 13, 2023 Non-Final Office Action dated Aug. 7, 2026.
U.S. Appl. No. 18/612,745, filed Mar. 21, 2024 Notice of Allowance dated Aug. 21, 2026.
U.S. Appl. No. 18/682,075, filed Feb. 7, 2024 Non-Final Office Action dated Jul. 16, 2026.
U.S. Appl. No. 18/682,082, filed Feb. 7, 2024 Advisory Action dated Aug. 27, 2026.
U.S. Appl. No. 18/682,082, filed Feb. 7, 2024 Final Office Action dated Jun. 11, 2026.
U.S. Appl. No. 18/701,916, filed Apr. 16, 2024 Notice of Allowance dated Aug. 25, 2026.
U.S. Appl. No. 18/826,105 filed Sep. 5, 2024 Non-Final Office Action dated Aug. 27, 2026.

* cited by examiner

SYSTEMS AND METHODS FOR ULTRASONICALLY MONITORING URINE OUTPUT

PRIORITY

This application claims the benefit of priority to U.S. Provisional Application No. 63/230,287, filed Aug. 6, 2021, which is incorporated by reference in its entirety into this application.

BACKGROUND

Nowadays, nearly all physiological parameters of a patient admitted to a critical care unit are sensed automatically by sophisticated commercial monitoring devices. This provides clinicians with invaluable information for interpreting the patient's state. In most cases, these devices can also supervise whether the values of the physiological parameters they sense remain within a pre-established range set by the clinician. This range represents the values considered as acceptable for each parameter. If a parameter does not fall within its acceptable range, audible warnings to alert the health care staff are generated. These devices discharge the healthcare staff of a considerable workload, since they need not continuously supervise whether the physiological parameters of every patient lie within the acceptable range. They also avoid human errors, which are common in any repetitive and monotonous task such as the supervision of physiological parameters.

It has been stated that the most relevant physiological parameter which is still measured and supervised manually by healthcare staff is urine output. Urine output is the best indicator of the state of the patient's kidneys. If the kidneys are producing an adequate amount of urine it means that they are well perfused and oxygenated. Otherwise, it is a sign that the patient is suffering from some complication. Urine output is required for calculating the patient's water balance, which is essential in the treatment of burn patients. Finally, it is also used in multiple therapy protocols to check whether the patient reacts properly to treatment. When urine output is too low the patient is said to have oliguria. If the patient does not produce urine at all, then he/she is said to have anuria. Sometimes, urine output can be too high; in these cases, the patient is said to have polyuria.

It is common to measure urine output by collecting urine in a graduated container. Periodically the nursing staff manually records the reading of the container of every patient, and operates a valve which releases the urine into a larger container. As such, the healthcare staff does not benefit from the advantages of having an automated determination and recording of urine output, or of the continuous and automatic supervision of its values. In critical care units, measurements of most every patient's urine output are often taken hourly, 24 times a day, 365 days a year. Furthermore, the monitoring of urine output for patients outside of the clinical setting is beneficial as well. As such urine collection devices that can be operated by the user/patient at home, for example, provide for urine output monitoring in the absence of a clinician. Transmitting the urine output data to the clinician provides for telemetric supervision of urine output values.

System and devices such as those described herein would decrease the workload associated with this collecting and monitoring urine output and, at the same time, permit supervision to take place on a more continuous basis resulting in better patient outcomes. Additionally, a compact system attached to the bed provides floor space for other medical equipment.

SUMMARY OF THE INVENTION

Briefly summarized, disclosed herein is a system for monitoring urine output of a patient. The system includes a collection canister and a drainage tube coupled with the canister, where the drainage tube defines a flow path for urine between the patient and the canister. The system further includes a display module coupled with the canister. The display module is configured to render urine output information on a display in accordance urine output collected within the canister, and the display module is coupled with and physically supported by the canister.

The canister may include an outlet port at the bottom end of the canister, the outlet port configured for draining urine from the canister. The outlet port may include a valve disposed in line with the outlet port, where the valve is configured for selective enabling and disabling of urine flow through the outlet port.

The canister includes a console having logic stored in memory that, when executed by one or more processors, causes performance of canister operations the include determining a volume of urine within the canister via a volume sensor of the canister. The volume sensor may include an ultrasonic sensor configured to determine a urine level within the canister, and the canister operations may further include determining the volume of urine from the urine level.

The display module also includes a console having logic stored in memory that, when executed by one or more processors, causes performance of display module operations that include wirelessly receiving urine volume data from the canister and rendering the urine volume data on the display. The display module operations may further include wirelessly transmitting the urine volume data across a network to an external entity, and the external entity may include an electronic medical record.

The display module operations may further include linking the urine volume data to the patient. In some embodiments, linking the urine volume data to the patient includes (i) receiving a unique identification of the patient, (ii) receiving a unique identification of the canister, and (iii) linking the unique identification of the canister to the unique identification of the patient.

The display module operations may further include purging urine volume data of a first patient from the memory of the display module prior to receiving urine volume data of a second patient.

In some embodiments, the system includes a preconnected tray, including the canister pre-coupled with the drainage tube to seal an internal volume from the environment, where the internal volume extends between a distal end of the drainage tube and a proximal end of the outlet port so that the canister pre-coupled with the drainage tube defines a closed system. The preconnected tray also includes (i) a sterile package enclosing the canister and a drainage tube, and (ii) a unique identification of the preconnected tray. In some embodiments, the preconnected tray further includes a catheter pre-coupled with the drainage tube, where the internal volume extends between a distal end of the catheter and a proximal end of the outlet port, and the canister pre-coupled with the catheter defines the closed system.

The canister may include a securement mechanism configured to anchor the canister to a bed of the patient, and the securement mechanism may include at least one deflectable member configured to extend at least partially around a bedrail of the bed. In some embodiments, the securement mechanism includes a tubing segment, where (i) the tubing segment includes a slot extending longitudinally along a flexible wall of the tubing segment between a first end and a second of the tubing segment, and (ii) the flexible wall defines the at least one deflectable member.

In some embodiments, the canister includes a horizontal bar attached to a front side of the canister and the display module includes an anchoring mechanism attached to a back side of the display module. The anchoring mechanism is configured to selectively attach the display module to the horizontal bar and detach the display module from the horizontal bar.

In use, the display module may be connected to a facility power source and in some embodiments, the display module includes a backup battery to power the display module when the facility power is interrupted.

The canister includes a canister battery configured to provide power to the volume sensor, and the canister battery may be sized to provide power to the volume sensor over a lifetime of canister use.

Also disclosed herein is a method of monitoring urine output of a patient. The method includes inserting a urinary catheter within the patient and coupling the patient to a urine output monitoring system, where the system includes a drainage tube pre-coupled with a canister. The method further includes anchoring the canister to a bed of the patient and anchoring the display module to the cannister, wherein the canister physically supports the display module. The method further includes establishing a flow of urine from the patient to the canister and measuring a volume of urine within the canister over a time period via a volume sensor of the canister. The method further includes (i) converting urine volume measurements into urine output data, (ii) transmitting the urine output data to the display module, and (iii) rendering the urine output data on a display of the display module. In some embodiments of the method, the urine output monitoring system further includes the catheter pre-coupled with the drainage tube.

In some embodiments, the method includes transmitting the urine output data across a network to an external entity, where the external entity includes an electronic medical record.

In some embodiments of the method, the volume sensor includes an ultrasonic sensor configured to determine a distance between a top of the canister and a top surface of the urine within the canister, and in some embodiments, coupling the display module to the canister includes defining a wireless communicative connection between the canister and the display module.

The method may further include (i) transmitting a unique identification of the canister to the display module, (ii) inputting a unique identification of the patient into the display module, and (iii) linking the unique identification of the canister to the unique identification of the patient.

Anchoring the canister to the bed of the patient may include extending at least one deflectable member of the canister at least partially around a bedrail of the bed, and anchoring the display module to the canister may include extending at least one deflectable member of the display at least partially around a horizontal bar attached to a front side of the canister.

The method may include purging urine volume data of a first patient from memory of the display module prior to transmitting the urine output data of a second patient to the display module.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1:
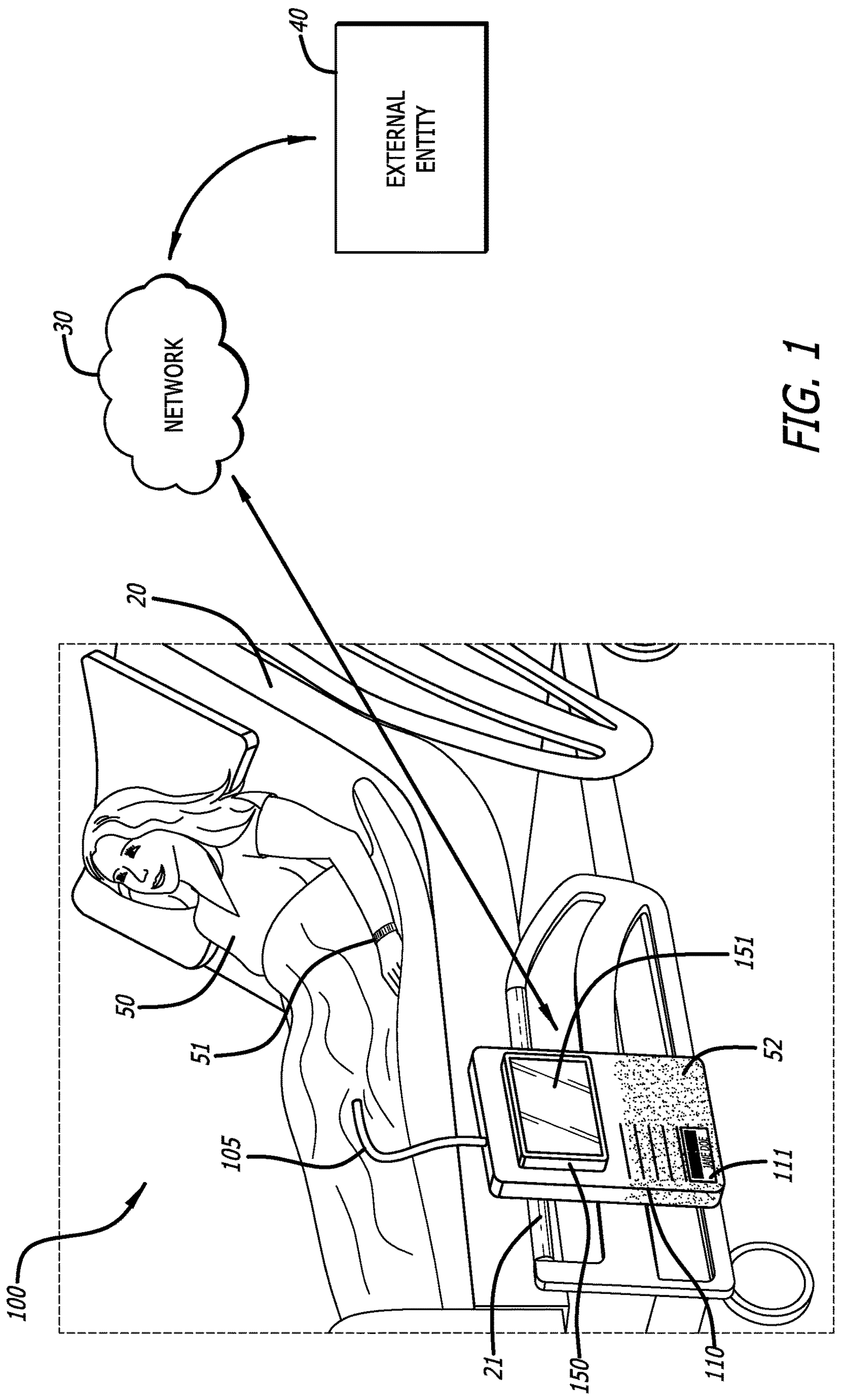
FIG. 1 illustrates an embodiment of a urine output monitoring system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words “including,” “has,” and “having,” as used herein, including the claims, shall have the same meaning as the word “comprising.” Furthermore, the terms “or” and “and/or” as used herein are to be interpreted as inclusive or meaning any one or any combination. As an example, “A, B or C” or “A, B and/or C” mean “any of the following: A; B; C; A and B; A and C; B and C; A, B and C.” An exception to this definition will occur only when a combination of elements, components, functions, steps or acts are in some way inherently mutually exclusive.

The phrases “connected to” and “coupled to” refer to any form of interaction between two or more entities, including mechanical, electrical, magnetic, electromagnetic, fluid, signal, communicative (including wireless), and thermal interaction. Two components may be connected or coupled to each other even though they are not in direct contact with each other. For example, two components may be coupled to each other through an intermediate component.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

The directional terms “proximal” and “distal” are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

Unless defined otherwise, all technical and scientific terms used herein have the same meaning as commonly understood by those of ordinary skill in the art.

FIG. 1 illustrates an embodiment of a urine output (UO) monitoring system, in accordance with some embodiments disclosed herein. The UO system 100 is generally configured to automatically collect and monitor UO from a patient 50. The UO system 100 is further configured to automatically record UO data and share the UO data across a network 30 with an external entity 40. The UO system 100 generally includes a canister 110 for the collection of urine 52 selectively coupled with a display module 150. The UO system 100 is further configured to uniquely link an identification 111 of the canister 110 with an identification 51 of the patient 50, thereby establishing the canister 110 as the patient identifier.

The canister 110 is selectively attachable to a bed 20, such as a bed rail 21, for example. Attaching the canister 110 to the bed 20 provides for co-location of the cannister 110 with the bed 20 which may be beneficial when the bed 20 is moved, such as between rooms, for example. The physical attachment of the canister 110 to the bed 20 further links the canister 110 with the patient 50. In some embodiments, the canister 110 may be a single use device (i.e., used for only one urine collection procedure). In other embodiments, the canister may be used for multiple urine collection procedures. Similarly, the canister 110 may be configured for use with a single patient, while in other embodiments, the cannister 110 may be configured for re-use across multiple patients The canister 110 is fluidly coupled with a bladder of the patient 50 via a drainage tube 105 so that urine 52 flows through the drainage tube 105 to the canister 110. The canister 110 includes a canister console 115 coupled with a volume sensor 116. The cannister console 115 and the volume sensor 116 provide for automatically measuring and recording of a volume of urine 52 within the canister 110.

The display module 150 is communicatively coupled with the canister 110. The display module 150 is configured provide UO monitoring data/information to a clinician via a display 151, e.g., a graphical user interface (GUI). The display module 150 may be configured to wirelessly couple with the canister 110. In other embodiments, the display module 150 may be coupled with the canister 110 via a wired connection. The display module 150 is selectively attachable to the canister 110 so that, when attached together, the canister 110 and the display module 150 may be handled as a single unit. When attached, the display module 150 is physically supported by the canister 110 (e.g., hangs on the canister 110).

In use, the clinician may catheterize the patient 50 and connect a catheter to the drainage tube 105. The clinician may attach the canister 110 to the bed 20. The clinician may attach the display module 150 to the canister 110 and establish a drainage flow of urine 52 from the patient 50 to the canister 110. The UO system 100 may automatically measure and record the volume of urine 52 within the canister 110 to define UO data for the patient 50. The display module 150 may transmit the UO data to the external entity 40 across the network 30.

The network 30 represents the communication pathways between the UO system 100 and the external entity 40. In one embodiment, the network 30 is the Internet. The network 30 can also utilize dedicated or private communication links (e.g., WAN, MAN, or LAN) that are not necessarily part of the Internet. The network 30 may use standard communications technologies and/or protocols.

The external entity 40 may be a person, an institution, or a cloud computing environment (e.g., cloud computing resources accessible via a network such as the internet). In some embodiments, the external entity 40 may include a healthcare provider. As such, it may be possible for the clinician or other healthcare professional to access UO information of the UO system 100 and thereby remotely monitor the UO condition of the patient 50. In some embodiments, the UO system 100 may be configured to alert the external entity 40 of an extreme UO condition or trend.

In some embodiments, the external entity 40 may include access to an electronic medical record (EMR) of the patient 60. In such embodiments, the EMR may automatically record UO information for review by the healthcare provider.

Those of skill in the art will appreciate that the UO system 100 may contain other architectural modules that are not described herein. In addition, conventional elements, such as firewalls, authentication systems, payment processing systems, network management tools, load balancers, and so forth are not shown as they are not material to the invention.

Figure 2A:
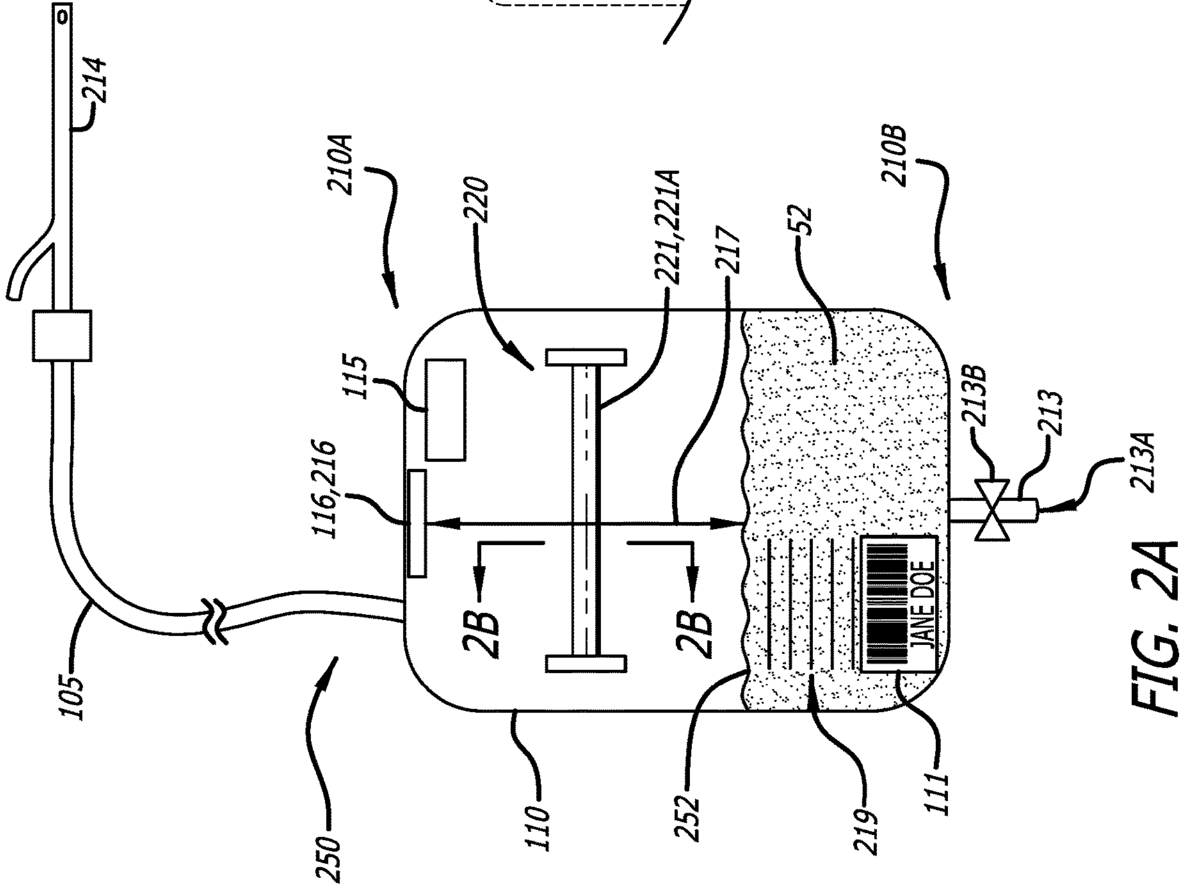
FIG. 2A illustrates a front view of a canister of the system of FIG. 1, in accordance with some embodiments.

FIG. 2A is a front view illustration of the canister 110, according to some embodiments. The canister 110 may be a hard-sided container or a flexible bag. As shown the drainage tube 105 is coupled with the canister 110 at a top end 210A of the canister 110. An outlet port 213 including a proximal end 213A is coupled with the canister 110 at a bottom end 210B. The outlet port 213 is configured to drain urine 52 from the canister 110. A valve 213B is disposed in line with the outlet port 213 to provide for selective enabling and disabling of flow of urine 52 through the outlet port 213.

The volume sensor 116 is coupled to the canister 110 at the top end 210A. The volume sensor 116 may generally function as a proximity sensor configured to measure a distance 217 between a level 252 (i.e., the top surface) of the urine 52 within the canister 110 and the top end 210A of the canister 110. In the illustrated embodiment, the volume sensor 116 includes an ultrasonic sensor 216. The volume sensor 116 provides an electrical signal to the cannister console 115 in accordance with the distance 217. The distance 217 may then be correlated with a volume of urine 52 within the canister 110 in accordance with the dimensions of the canister 110. The canister 110 may include indica 219. The indica 219 may include volume indications, such as graduation lines, for example. The indica 219 may also include the identification 111 of the cannister 110, such as a serial number, for example.

The canister 110 may define a volume capacity to allow urine 52 to be collected and measured over an extend period of time (e.g., about 1-2 days) without draining the urine 52 from the canister 110. In some embodiments, the canister 110 may define a volume capacity exceeding about 1 liter, 2 liters, 3 liters or more.

In some embodiments, the canister 110 and the drainage tube 105 may be combined to define a closed system 250. The closed system 250 may include the drainage tube 105 pre-attached to the canister 110 so that the internal space extending between a distal end 105A of the draining tube 105 and the proximal end 213A of the outlet port 213 is sealed (i.e., completely closed off) against the environment. In some embodiments, the closed system 250 may also include the catheter 214. In some embodiments, the drainage tube 105 may be permanently attached to the canister 110. In other embodiments, the drainage tube 105 may be detachable from the canister 110. Similarly, in some embodiments, the catheter 214 may be permanently attached to the drainage tube 105. In other embodiments, the catheter 214 may be detachable from the drainage tube 105.

Figure 2B:
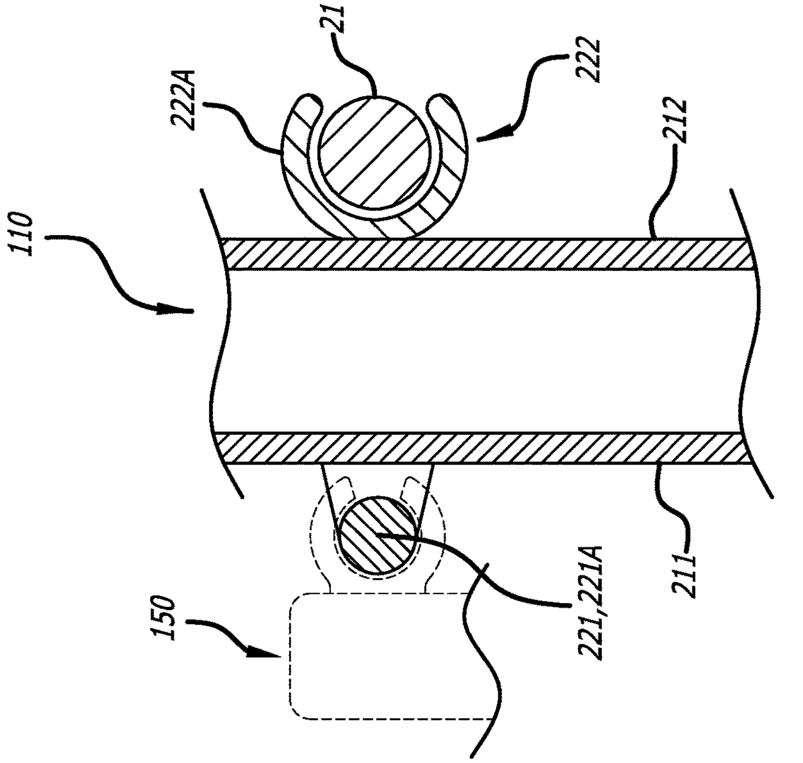
FIG. 2B is a cross-sectional side view of a portion of the canister of FIG. 2A, in accordance with some embodiments.

FIG. 2B illustrates a side cross-sectional view of a portion of the canister 110 cut along sectioning lines 2B-2B, in accordance with some embodiments. With reference to FIGS. 2A and 2B, the canister is configured to attach to both the display module 150 and the bed 20. The canister 110 includes a first portion 221 of an attachment mechanism 220 configured to facilitate selective attachment of the canister 110 to the display module 150. In an exemplary embodiment, the first portion 221 includes a bar 221A horizontally attached to a front canister wall 211. The bar 221A is configured to engage a second complementary portion of the attachment mechanism 220 as further described below.

The canister 110 also includes a bed attachment mechanism 222, which in some embodiments, may be disposed on a back wall 212 of the canister 110. The bed attachment mechanism 222 is configured to secure the canister 110 to the bed rail 21 of the bed 20. In one exemplary embodiment, the bed attachment mechanism 222 includes one or more deflectable members 222A configured to extend partially around the bed rail 21. In some embodiments, the deflectable members 222A may in some respects resemble a C-clip or a hinge-type clamp. In use, the deflectable members 222A are deflected outward allowing the bed attachment mechanism 222 to receive the bed rail 21. Thereafter, the deflectable members 222A self-deflect inward to retain the bed rail 21 between deflectable members 222A. In some embodiments, the deflectable members 222A may be defined by a tubing segment (not shown) having a slot extending longitudinally along a flexible tubing wall, where in use, the bed rail 21 is secured within a lumen of the tubing segment. In other embodiments, the bed attachment mechanism 222 may include hooks, screw clamps, or any other suitable attachment mechanisms.

Figure 3:
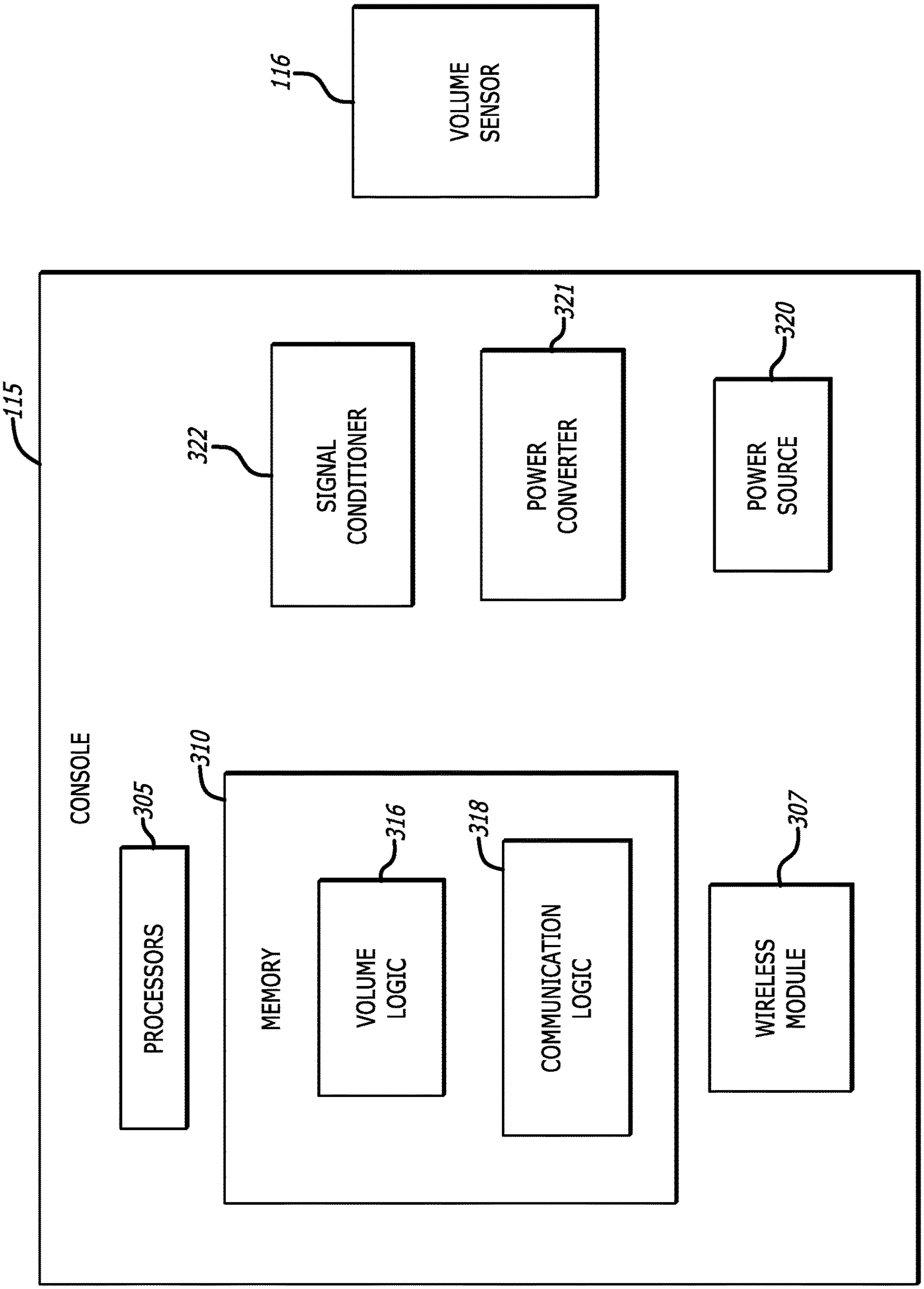
FIG. 3 is a block diagram of a console of the canister of FIG. 2A, in accordance with some embodiments.

FIG. 3 illustrates a block diagram of the canister console 115 of FIG. 1, in accordance with some embodiments. The cannister console 115 includes one or more processors 305 and memory 310 including a non-transitory, computer-readable storage medium. Stored in the memory 310 are volume logic 316 and communication logic 318. A power source 320 provides electrical power to the cannister console 115 including the console components and the volume sensor 116. The volume sensor 116 is coupled with the cannister console 115. A signal conditioner 322 converts electrical signals from the volume sensor 116 to digital signals for processing by the volume logic 316. The electrical power passes through a power converter 321 to facilitate the operation of the volume sensor 116. A wireless module 307 facilitates communication and data sharing with the display module 150.

The power source 320 may be an internal battery and the battery may be configured to provide sufficient power over the entire life of the canister 110. In some embodiments, the power source 320 may be a battery that is connectable to the facility power source for recharging. In other embodiments, the power source 320 may be an external facility power source. The power converter 321 converts the electrical power from the power source 320 into forms of electrical power compatible with the volume sensor 16 and other console components.

The volume logic 316 is configured to control the volume sensor 116 and electrical signals received from the volume sensor 116. The volume logic 316 may also control the power converter 321 to enable/disable the volume sensor 116. The volume logic 316 receives digital signals from the volume sensor 116 via the signal conditioner 322 and processes the digital signals into volume data. The volume logic 316 records and prepares the volume data for transfer to the display module 150 via the wireless module 307.

The communication logic 318 facilitates data transfer between the canister 110 and the display module 150. The canister 110 includes a unique identification 111 of the canister 110. The canister identification 111 may include a series of alpha and/or numerical characters. In some embodiments, the unique identification 111 may be a name or a model/serial number which may be printed or otherwise displayed on the canister 110. The communication logic 318 may sync/link the volume data from the volume logic 316 with the unique identification 111.

Figure 4B:
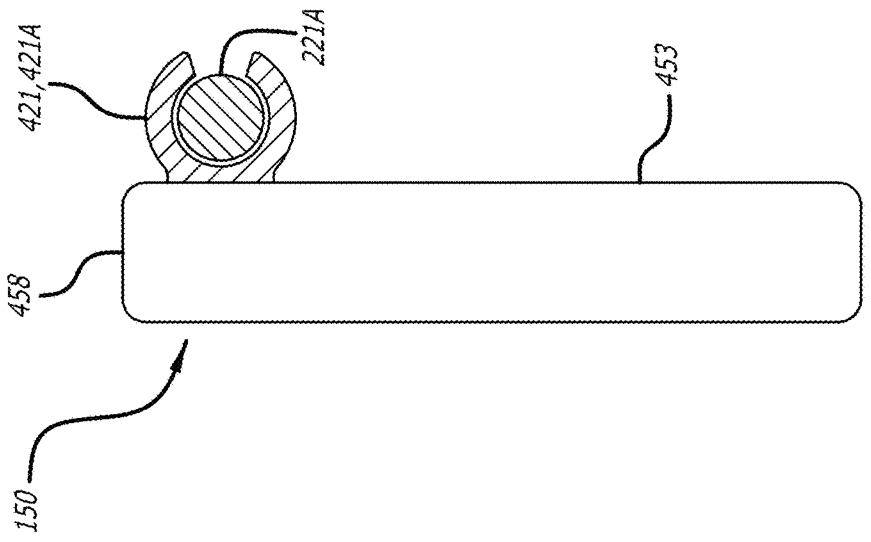
FIG. 4B is a cross-sectional side view of the display module of FIG. 4A, in accordance with some embodiments.
Figure 4A:
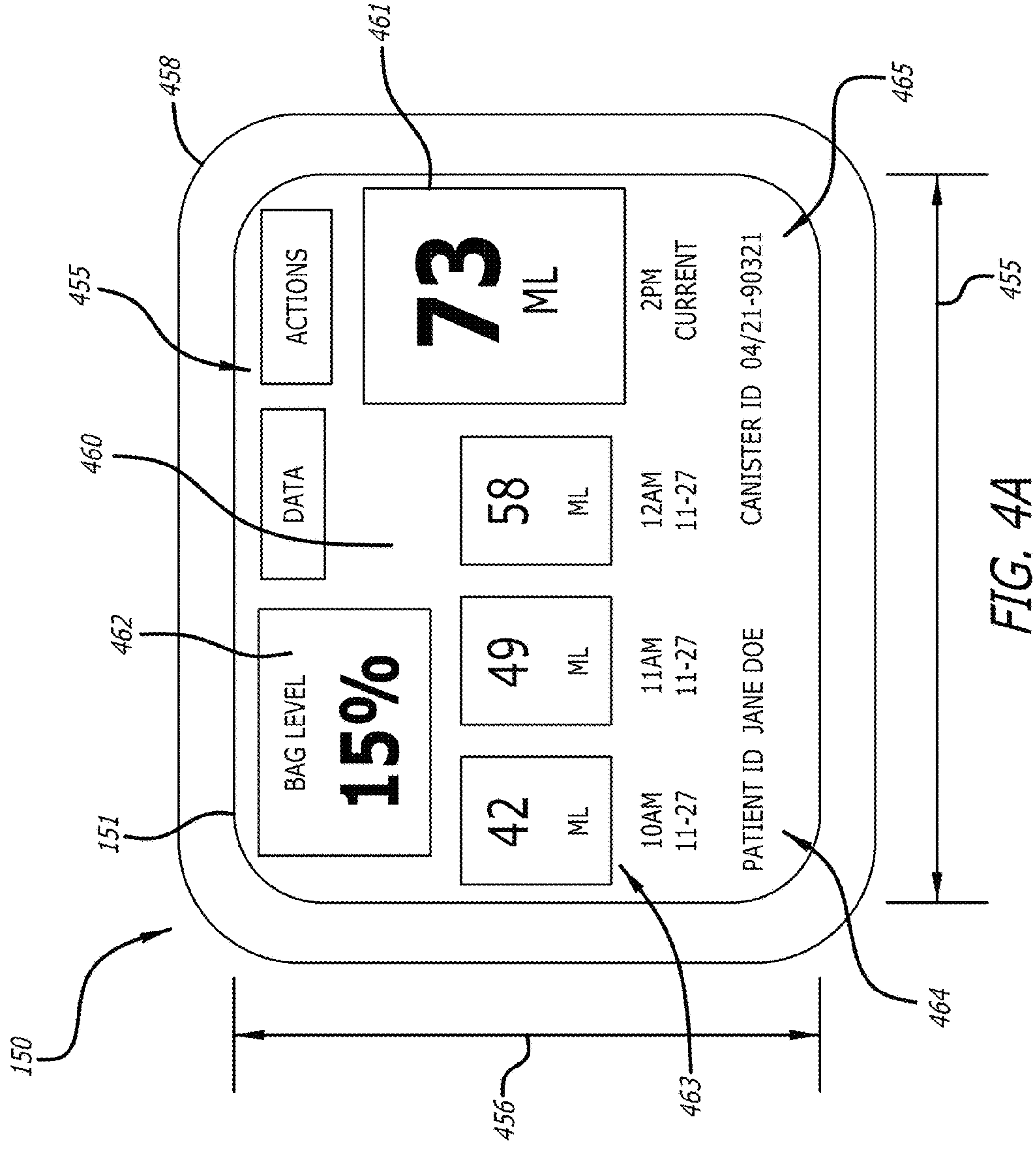
FIG. 4A illustrates a front view of a display module of the system of FIG. 1, in accordance with some embodiments.

FIGS. 4A and 4B further illustrate the display module 150 of FIG. 1, in accordance with some embodiments. FIG. 4A is a front view of the display module 150 and FIG. 4B is a right-side view of the display module 150. In some embodiments, the display module 150 may be a compact device, that may in some respects resemble a tablet computing device, having the display 151 and a module console 455 disposed with a housing 458. The display 151, which may also be a graphical user interface (GUI), is disposed on the front side of the display module 150. The display 151 may generally define a rectangular shape having a width dimension 455 and a height dimension 456. In some embodiments, the width dimension 455 and a height dimension 456 may be defined such the information rendered on the display 151 is readable from a distance of about 5 to 10 feet away, i.e., a distance across a patient room. More specifically, the width dimension 455 and the height dimension 456 may be between about 100 mm and 300 mm, for example.

The display module 150 includes a second complementary portion 421 of the attachment mechanism 220 to facilitate attachment of the display module 150 to the cannister 110. In one exemplary embodiment, the second complementary portion 421 is coupled to a back wall 453 of the housing 458. The second complementary portion 421 is configured to selectively couple with the first portion 221 of the attachment mechanism 220, i.e., the bar 221A. The second complementary portion 421 may in many respects resemble the features and functionality of the attachment mechanism 222 of FIG. 2B. As such, the second complementary portion 421 may include the deflectable members 421A that in some respects may resemble a C-clip or a hinge-type clamp, for example. In use, the deflectable members 421A are deflected outward allowing the second complementary portion 421 to receive the bar 221A. Thereafter, the deflectable members 421A self-deflect inward to retain the bar 221A between deflectable members 421A. In some embodiments, the deflectable members 421A may be defined by a tubing segment (not shown) having a slot extending longitudinally along a flexible tubing wall, so that in use, the bar 221A is secured within a lumen of the tubing segment. In other embodiments, the second complementary portion 421 may include hooks, screw clamps, or any other suitable attachment mechanisms.

In use, the display 151 may render UO related data/information thereon, such as illustrated in the exemplary screen shot 460 depicted in FIG. 4A, for example. Exemplary, information may include a current volume 461 of urine 52 collected within the cannister 110. In some instances, it may be advantageous for the clinician to observe the current volume 461 from across the patient room. As such, the font size of the current volume 461 may be greater than (and in some embodiments substantially greater than) other information rendered on the display 151. Other exemplary volume related information may include a current bag level 462 occupied by urine 52 and a recent history of recorded urine volumes 463.

In some instances, it may be advantageous for the clinician to verify that the unique identification 51 of the patient 50 and the unique identification 111 of the canister 110 are properly linked. Hence, other exemplary information rendered on the display 151 may include the unique identification 51 of the patient 50 and the unique identification 111 of the canister 110. As stated above, the display 151 may include a GUI so that the clinician may enter information into the display module 150 directly.

Figure 5:
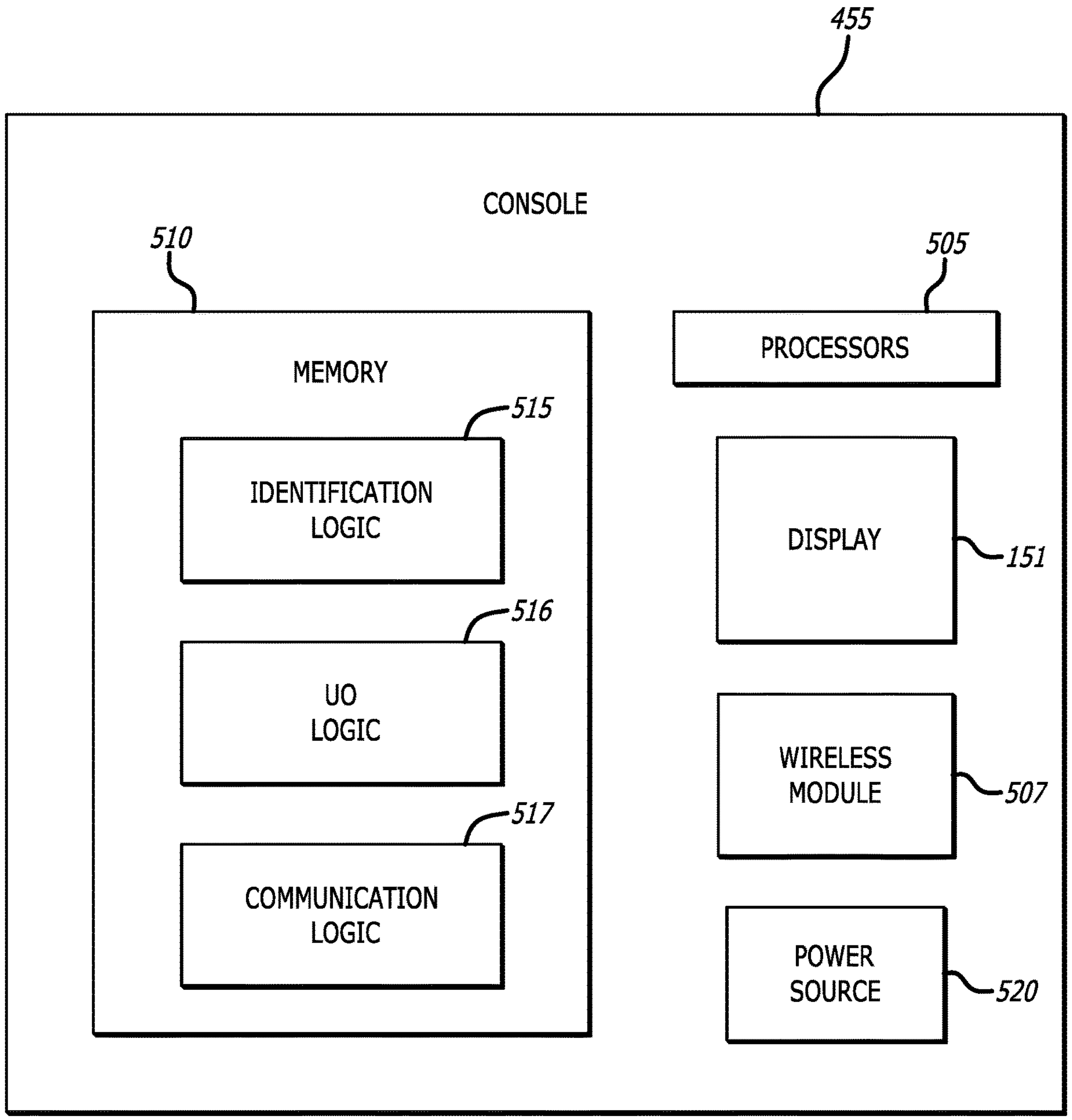
FIG. 5 is a block diagram of a console of the display module of FIG. 4A, in accordance with some embodiments.

FIG. 5 illustrates a block diagram of the module console 455 of FIG. 4A, in accordance with some embodiments. The module console 455 includes one or more processors 505 and memory 510 including a non-transitory, computer-readable storage medium. Stored in the memory 510 are identification logic 515, UO logic 516 and communication logic 517. A power source 520 provides electrical power to the console 455 including the console components. The power source 520 may be an external facility power source to which the display module 150 is connected for use. In some instances of use, it may be necessary to disconnect the display module 150 from the power source 520 such as when display module 150 is moved between beds/rooms and/or when the patient 50 is located in an operating room, where access to the power source 520 is not convenient. As such, in some embodiments, the power source 520 may include an internal backup battery (not shown) to provide power while the display module 150 is disconnected from the facility power source. In other embodiments, the power source 520 may include a battery as a primary power source. In such an embodiment, display module 150 may connect to the facility power source as a backup source and/or to recharge the battery.

A wireless module 507 facilitates communication and data sharing between the display module 150 and canister 110. The wireless module 507 may also facilitate communication and data sharing between the display module 150 and the external entity 40 across the network 30.

The identification logic 515 uniquely links the patient 50 to the cannister 110. More specifically, the identification logic 515 uniquely links the unique identification 51 of the patient 50 to the unique identification 111 of the cannister 110 so that UO data received from the cannister 110 is linked to the patient 50. The display module 150 may learn the unique identification 51 of the patient 50 via direct input by the clinician, from the external entity 40, or via a QR code/RFID tag coupled with the patient 50 or the like. The identification logic 515 may also link the UO data with other pertinent information such as the date and time of the UO data.

The UO logic 516 may be configured to process UO data received from the canister 110. The UO logic 516 may populate display screens with UO information pertinent to the monitoring of the UO for the patient 50. The UO logic 516 may define a record of the UO data for the patient 50. The UO logic 516 may also calculate statistical values from the UO data, such as a rate of UO, maximum and minimum rates of UO, and any other statistical values suitable for assessing a urinary health status of the patient 50. The UO logic 516 may manage the UO data stored in the memory 510, such as archiving UO records over a defined time period, and/or purging UO records from the memory 510 after transmitting the UO information to the external entity, for example.

The communication logic 517 defines the communication between the display module 150 and the cannister 110 which may include establishing a wireless communication link (e.g., a pairing) between the display module 150 and the cannister 110. In some instances, more than one cannister 110 and more than one display module may be located within a pairing environment. As such, in some embodiments, communication logic 517 may be configured to uniquely pair the display module 150 with one and only one canister 110, such as the canister 110 in closest proximity to the display module 150, for example. The wireless communication between the display module 150 and the canister 110 employ any suitable wireless protocol, e.g., Bluetooth, radio frequency, infrared, microwave, Zigbee, or the like. The communication logic 517 may also manage the wireless communication between the display module 150 and the external entity 40 across the network 30.

In some embodiments, when the display module 150 is communicatively coupled with a canister 110, the identification logic 515 may define an inquiry regarding the unique identification 51 of the patient 50. More specifically, the identification logic 515 may ask the user to indicate if the coupled canister 110 should be linked with the previous patient 50 or a new patient 50. In the instance of the previous patient 50, the identification logic 515 may link the unique identification 111 of the canister 110 with the unique identification 51 of the previous patient 50 so that the UO data to be received is linked with the previous patient 50, and so that statistical values (e.g., trending) continue from the previously received UO data to the UO data to be received. In the instance of a new patient, the identification logic 515 or the UO logic 515 may purge all previously recorded UO data from the display module 150 in preparation to receive UO data for the new patient 50.

In the illustrated embodiment, any or all of the identification logic 515, the UO logic 516 and the communication logic 517 may be in the form of a software application that is loaded on the UO system 100 and executable by the one or more processors 505. In other embodiments, each of the identification logic 515, the UO logic 516 and the communication logic 517 or portions thereof, need not be loaded on the display module 150 but may instead execute within a cloud computing environment (which may also be represented by the reference numeral 30) such that UO data obtained by the UO monitoring system 100 are communicated to the identification logic 515 and/or the UO logic 516 for processing. Thus, the communication logic 517 represented as being part of the display module 150 may include an application programming interface (API) that is configured to transmit and receive data communication messages to and from the identification logic 515 and/or the UO logic 516 operating in the cloud computing environment.

Figure 6:
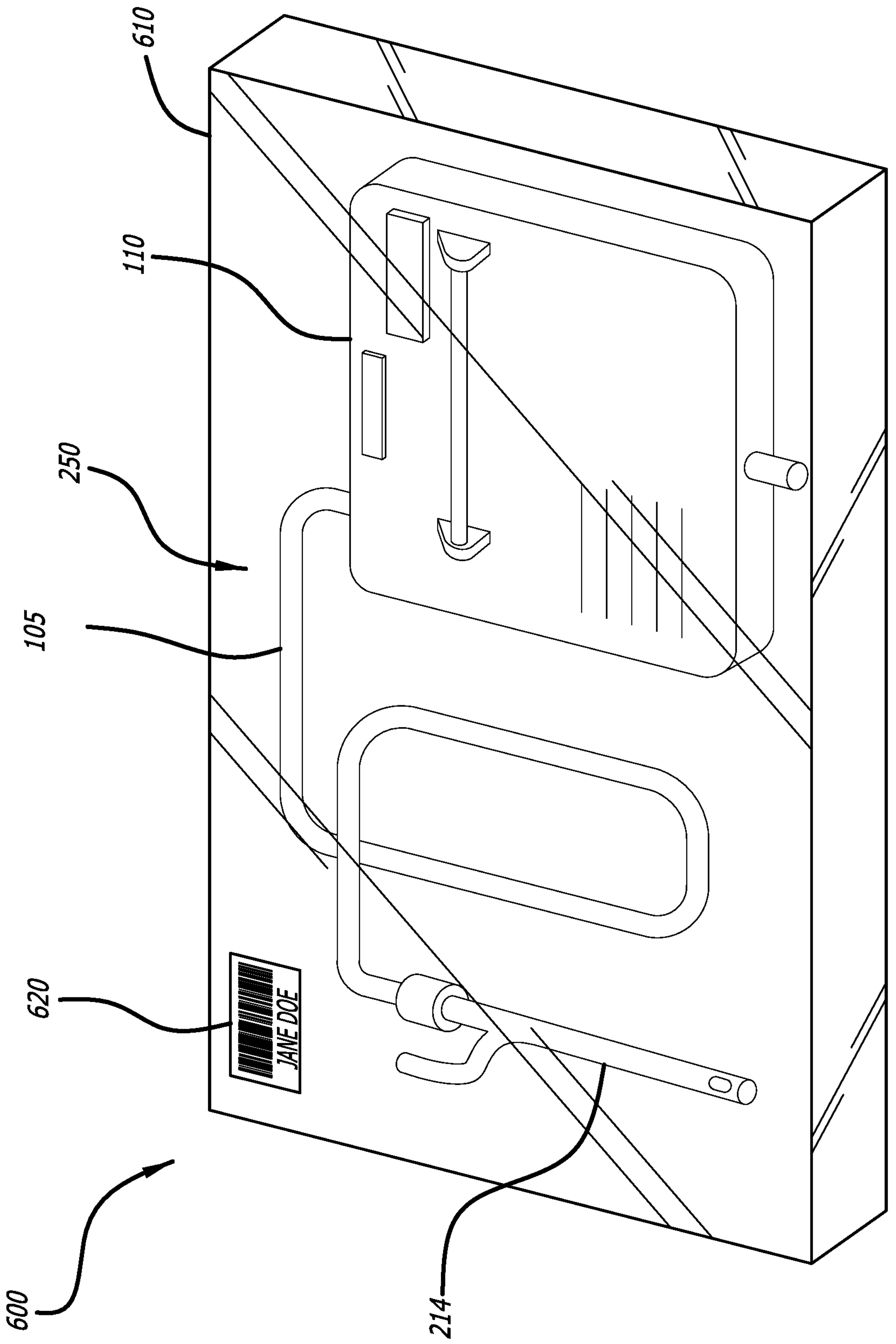
FIG. 6 is a perspective illustration of an embodiment of a preconnected tray of the system of FIG. 1, in accordance with some embodiments.

FIG. 6 illustrates a preconnected tray of the system of FIG. 1, in accordance with some embodiments. The preconnected tray 600 includes a sterile package 610 sealably enclosing the closed system 250. As described above, in some embodiments, the closed system 250 may include the catheter 214, and in alternative embodiments, the closed system 250 may omit the catheter 214. The closed system 250 may be disposed within the sterile package 610 after which the preconnected tray 600 may be sterilized.

The preconnected tray 600 includes a unique tray identification 620 of the preconnected tray 600, thereby establishing the preconnected tray 600 and the canister 110 included therein as the patient identifier. The unique tray identification 620 may include a series of alpha and/or numerical characters. In some embodiments, the unique tray identification 620 may be a name or a model/serial number which may be printed or otherwise displayed preconnected tray 600. The communication logic 318 may sync/link the volume data from the volume logic 316 with the unique tray identification 620.

A method of monitoring the UO of a patient may include the following steps or process. The clinician may insert the urinary catheter 214 within a patient to access urine 52 within the bladder of the patient. The clinician may also connect the drainage tube 105 to the catheter 214. In some embodiments, the drainage tube 105 may be preconnected to the catheter 214. The clinician may anchor the canister 110 to a bed 20 of the patient 50 which may include attaching the canister 110 to the bedrail 21 of the bed 20. The clinician may also anchor the display module 150 to the cannister 110 so that the canister 110 physically supports the display module 150. In some embodiments, the clinician may couple an attachment mechanism 421 on the back side of the display module 150 to a horizontal bar 221A disposed on a front side of the canister 110. The clinician may establish a flow of urine from the patient 50 to the canister 110 and the canister 110 may measure a volume of urine 52 within the canister 110 over a time period via a volume sensor 116 of the canister 110. Measuring the volume of urine 52 may include ultrasonically determining a distance 217 between an ultrasonic sensor 216 at the top end 210A of the canister 110 and a top surface of the urine 52 within the canister 110. The method of may further include coupling the display module 150 to the canister 110 via a wireless communicative connection.

The method may further include transmitting urine volume measurements from the canister 110 to the display module 150 and converting the urine volume measurements into urine output data. The method may further include rendering the urine output data on a display of the display module. The urine output data may also be transmitted across a network 30 to an external entity 40 and the external entity 40 may include an electronic medical record.

The method may further include transmitting a unique identification 111 of the canister 110 from the canister 110 to the display module 150. The method may further include inputting a unique identification 51 of the patient 50 into the display module 150 and linking the unique identification of the canister to the unique identification of the patient.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A system for monitoring urine output of a patient, comprising:

a canister assembly, comprising:

a canister configured to collect a volume of urine from the patient, the canister including a unique canister identification; and a canister console coupled with the canister, the canister console including canister logic stored in canister memory that, when executed by one or more canister processors, causes performance of canister operations, including:

determining the volume of urine within the canister via a volume sensor of the canister, and linking the volume of urine with the unique canister identification;

a drainage tube coupled with the canister, the drainage tube defining a flow path for urine between the patient and the canister; and a display module coupled with the canister assembly, the display module configured to render urine output information on a display in accordance with urine output collected within the canister, wherein the display module is coupled with the canister, and physically supported by the canister, wherein the display module comprises a display console including display logic stored in display memory that, when executed by one or more display processors, causes performance of display module operations including:

receiving a unique identification of the patient;

receiving the unique canister identification from the canister assembly; and linking the unique canister identification to the unique identification of the patient.

2. The system according to claim 1, wherein:

the canister includes an outlet port at a bottom end of the canister, the outlet port configured for draining urine from the canister, and a valve disposed in line with the outlet port, the valve configured for selective enabling and disabling of urine flow through the outlet port.

3. The system according to claim 1, wherein:

the volume sensor includes an ultrasonic sensor configured to determine a urine level within the canister, and the canister operations further include determining the volume of urine from the urine level.

4. The system according to claim 1, wherein:

the canister assembly includes a canister battery configured to provide power to the volume sensor, and the canister battery is sized to provide power to the volume sensor over a lifetime of canister assembly use.

5. The system according to claim 1, wherein the display module operations further include:

wirelessly receiving urine volume data from the canister assembly; and rendering the urine volume data on the display.

6. The system according to claim 5, wherein the display module operations further include wirelessly transmitting the urine volume data across a network to an external entity.

7. The system according to claim 6, wherein the external entity includes an electronic medical record.

8. The system according to claim 5, wherein the display module operations further include linking the urine volume data to the patient.

9. The system according to claim 5, wherein the display module operations include purging the urine volume data of a first patient from the display memory of the display module prior to receiving the urine volume data of a second patient.

10. The system according to claim 9, further comprising a preconnected tray, the preconnected tray comprising:

the canister pre-coupled with the drainage tube to seal an internal volume from an environment, the internal volume extending between a distal end of the drainage tube and a proximal end of an outlet port, the canister pre-coupled with the drainage tube defining a closed system, a sterile package enclosing the closed system, and a unique identification of the preconnected tray.

11. The system according to claim 10, wherein:

the preconnected tray further comprises a catheter pre-coupled with the drainage tube, the internal volume extends between a distal end of the catheter and the proximal end of the outlet port, and the canister pre-coupled with the catheter defines the closed system.

12. The system according to claim 1, wherein the canister comprises a securement mechanism configured to anchor the canister to a bed of the patient.

13. The system according to claim 12, wherein the securement mechanism comprises:

a first deflectable member extending away from the canister and around a top side of a bedrail of the bed when the canister is anchored to the bed; and a second deflectable member extending away from the canister and around a bottom side of the bedrail.

14. The system according to claim 13, wherein: the securement mechanism includes a tubing segment having a first side attached to the canister, the tubing segment includes a slot extending longitudinally along a flexible wall of the tubing segment between a first end and a second end of the tubing segment, the slot disposed along a second side of the tubing segment opposite the first side, and the flexible wall defines the first deflectable member and the second deflectable member.

15. The system according to claim 1, wherein:

the canister includes a horizontal bar coupled with and disposed away from a front side of the canister; and the display module comprises an anchoring mechanism attached to a back side of the display module, the anchoring mechanism configured to selectively attach the display module to the horizontal bar, and detach the display module from the horizontal bar.

16. The system according to claim 1, wherein in use, the display module is connected to a facility power source.

17. The system according to claim 16, wherein:

the display module includes a backup battery, and the backup battery powers the display module when the facility power source is interrupted.

18. The system according to claim 1, wherein the unique canister identification includes a serial number of the canister.

19. The system according to claim 1, wherein the unique canister identification is printed on the canister.

20. The system according to claim 1, wherein the display module operations further include:

linking the unique canister identification to a unique identification of a first patient, and subsequently linking the unique canister identification to a unique identification of a second patient.

21. A method of monitoring urine output of a patient, comprising:

inserting a urinary catheter within the patient;

coupling the patient to a urine output monitoring system, the urine output monitoring system comprising:

a drainage tube;

a canister assembly, comprising:

a canister pre-coupled with the drainage tube, the canister including a unique canister identification;

a canister console coupled with the canister, the canister console including canister logic stored in cannister memory that, when executed by one or more canister processors, causes performance of canister operations; and a display module coupled with the canister, the display module including a display console including display logic stored in display memory that, when executed by one or more display processors, causes performance of display module operations;

anchoring the canister to a bed of the patient;

anchoring the display module to the canister, wherein the canister physically supports the display module;

establishing a flow of urine from the patient to the canister;

measuring a volume of urine within the canister over a time period via a volume sensor of the canister;

converting urine volume measurements into urine output data via the canister operations;

transmitting the urine output data to the display module via the canister operations;

rendering the urine output data on a display of the display module via the display module operations;

transmitting the unique canister identification to the display module via the canister operations;

inputting a unique identification of the patient into the display module;

linking the unique canister identification to the unique identification of the patient via the display module operations, and linking the urine output data to the unique canister identification via the canister operations.

22. The method according to claim 21, further comprising transmitting the urine output data across a network to an external entity.

23. The method according to claim 22, wherein the external entity has stored thereon an electronic medical record.

24. The method according to claim 21, wherein the volume sensor comprises an ultrasonic sensor configured to determine a distance between a top of the canister and a top surface of the urine within the canister.

25. The method according to claim 21, wherein coupling the display module to the canister assembly comprises defining a wireless communicative connection between the canister and the display module.

26. The method according to claim 21, wherein anchoring the canister to the bed of the patient comprises extending at least one deflectable member of the canister at least partially around a bedrail of the bed.

27. The method according to claim 21, wherein anchoring the display module to the canister comprises:

extending at least one deflectable member of the display module at least partially around a horizontal bar attached to a front side of the canister, and extending at least one other deflectable member of the display module at least partially around a bottom side of the horizontal bar.

28. The method according to claim 21, further comprising purging urine volume data of a first patient from the display memory prior to transmitting the urine output data of a second patient to the display module.

29. The method according to claim 21, wherein the urine output monitoring system further comprises the urinary catheter pre-coupled with the drainage tube.

* * * * *